(12) United States Patent
Fankhauser et al.

(10) Patent No.: US 8,871,243 B2
(45) Date of Patent: Oct. 28, 2014

(54) DISINTEGRABLE ORAL FILMS

(75) Inventors: Christopher Edward Fankhauser, Eagle, NE (US); Greg Slominski, Elmwood, NE (US); Stephan Meyer, Geneva (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/329,390

(22) Filed: Dec. 19, 2011

(65) Prior Publication Data

US 2012/0125351 A1 May 24, 2012

Related U.S. Application Data

(63) Continuation of application No. 11/675,822, filed on Feb. 16, 2007, now abandoned.

(60) Provisional application No. 60/774,592, filed on Feb. 17, 2006.

(51) Int. Cl.
*A61F 2/00* (2006.01)
*A61K 9/00* (2006.01)
*A61K 9/70* (2006.01)

(52) U.S. Cl.
CPC ............... *A61K 9/7007* (2013.01); *A61K 9/006* (2013.01); *A61K 9/0056* (2013.01)

USPC .......................................................... 424/426

(58) Field of Classification Search
None
See application file for complete search history.

(56) References Cited

U.S. PATENT DOCUMENTS

2004/0156885 A1  8/2004  Zerbe et al.
2007/0059346 A1*  3/2007  Maibach ....................... 424/443

FOREIGN PATENT DOCUMENTS

| CN | 1514728 | 7/2004 |
| EP | 1430896 | 6/2004 |
| WO | WO 9600072 | 1/1996 |
| WO | WO 0180837 | 11/2001 |
| WO | WO 02/085119 | 10/2002 |
| WO | WO 2004/054551 | 7/2004 |

* cited by examiner

*Primary Examiner* — Paul Dickinson
(74) *Attorney, Agent, or Firm* — Larson & Anderson, LLC

(57) ABSTRACT

A water soluble film that is disintegrable in the oral cavity to deliver an active agent is provided. The disintegrable film includes at least one water soluble polymer and an active agent. Also provided are methods for preparing the disintegrable oral film and for using the disintegrable film to administer an effective dosage of an active agent into the oral cavity for absorption through the oral mucosa. According to certain embodiments, the disintegrable film includes at least one water soluble polymer and a nicotine active.

34 Claims, 1 Drawing Sheet

DISINTEGRABLE ORAL FILMS

This application claims the benefit of U.S. Provisional Application No. 60/774,592, filed Feb. 17, 2006.

The present invention relates to disintegrable oral films for the delivery and release of an active agent into the oral cavity. According to certain embodiments, the invention relates to a slow disintegrating oral film containing a nicotine active for delivery and release into the oral cavity. The slow disintegrating oral film maximizes the absorption of the nicotine active through the oral mucosa to alleviate cravings for nicotine.

BACKGROUND

Smoking of tobacco products, such as cigarettes, cigars, and pipe tobacco, presents serious health risks to the tobacco user. Additionally, the use of smokeless tobacco products, such as chewing tobacco (both short and broad leaf tobacco) and snuff, can also result in serious health risks to the user.

While the serious health risks associated with the use of tobacco products are well documented and widely publicized, many habitual users are unable to quit using the tobacco products. The inability to quit using tobacco products can be primarily attributed to the fact that the user has developed a dependence on the nicotine that is present in the tobacco products. The dependence on nicotine manifests itself as nicotine cravings. Accordingly, a nicotine addicted tobacco user must continually use tobacco products to replenish the amount of nicotine in the blood, thereby satisfying the nicotine craving.

In order to successfully quit using tobacco products, the nicotine addicted tobacco user must overcome the nicotine cravings, thereby diminishing the desire to use tobacco products. Certain nicotine replacement therapies have been developed to assist the habitual tobacco user to quit using tobacco products. These nicotine replacement therapies attempt to temporarily replace some of the nicotine in the blood that is lost when a habitual user quits using tobacco products.

Nicotine replacement therapies have been developed and are provided in a variety of product forms. Such nicotine replacement products include, for example, nicotine containing gums, nicotine containing inhalers, nicotine containing transdermal patches, nicotine containing lozenges, and nicotine containing lollipops. Nicotine containing gums, lozenges and patches have enjoyed substantial commercial success.

One commercially available nicotine containing gum product is available under the trademark NICORETTE. The nicotine containing gums are generally supplied as individual pieces of chewable gum. The user removes an individual piece of the nicotine containing gum from the package and places it into the oral cavity. While the user is chewing the gum, nicotine is released from the gum and is absorbed by the oral mucosa. The nicotine containing gums, however, must be used at regular intervals in order to maintain steady levels of nicotine in the blood.

Nicotine containing gums may be used to relieve acute cravings experienced by a tobacco user that is attempting to quit smoking or smoke-less tobacco product use. For example, a single piece of gum may be self-administered by an individual in response to an acute nicotine craving. Such use of the nicotine gum typically results in an increase in blood nicotine levels to counteract the nicotine cravings. The tobacco user must repeatedly self-administer nicotine containing gums to maintain steady nicotine levels in the blood.

Commercially available nicotine containing transdermal patches include, for example, NICODERM, NICOTROL, and HABITROL. The nicotine transdermal patches are generally supplied as a patch having an adhesive backing covered by a release liner to protect the adhesive. The user of the patch removes the release liner from the patch to expose the adhesive backing. The adhesive backing is then applied to a suitable location on the dermis of the user, thereby adhering the patch to the user. Over time, nicotine is released from the patch and diffuses through the dermis and into the blood. The nicotine containing transdermal patches are useful for maintaining relatively steady blood level concentrations over time by providing the user with a substantially continuous infusion of nicotine while the patch is being worn.

Nicotine containing lozenges may be utilized in a similar manner as nicotine containing gums to provide relief from acute nicotine cravings. Commercially available nicotine containing lozenges include, for example, those lozenges sold under the trademarks COMMITS, STOPPERS, NIQUITIN, and NICOTINELLS. Similar to the nicotine containing gums, a tobacco user, instead of choosing to use a tobacco product, may self-administer a nicotine containing lozenge to alleviate a nicotine craving.

While commercially available nicotine replacement products provide some level of alleviation of both steady and acute tobacco cravings, there is still an ongoing need to provide more effective craving relief and to assist the tobacco user in quitting use of the tobacco products.

Films for delivering a pharmacologically or cosmetically active agent via the oral cavity have been developed. The films generally comprise water soluble films that disintegrate in the oral cavity and release the active agent that is incorporated the film. Nicotine has been incorporated into water soluble films, which upon disintegration of the film, releases nicotine into the oral cavity. The prior art has focused on water soluble thin films for achieving rapid disintegration or dissolution in the oral cavity, in order to alleviate acute nicotine cravings. For these rapidly disintegrating films, studies estimate that systemic absorption of the nicotine active is merely 25% of the total amount of the nicotine active initially present in the oral film dosage unit. This low level of absorption of the nicotine active through the oral mucosa can be directly attributed to the rapid disintegration of the oral film, which does not permit sufficient time for mucosal permeation. Thus, the vast majority of the nicotine active present in the oral film is simply swallowed.

The prior art nicotine containing oral films, however, do not address the difficulty associated with maximizing absorption of the nicotine active through the oral mucosa. Thus, there remains a need in the art for a slower disintegrating oral film that disintegrates at a rate that maximizes the absorption of the nicotine active through the oral mucosa, which thereby effectively delivers a dose of nicotine active to a user in a sufficient amount to reduce or eliminate nicotine cravings associated with the cessation of tobacco usage.

SUMMARY

An oral film for delivering and releasing an active agent into the oral cavity is provided. The composition of the oral film provides a mucoadhesive film having a delayed or slow disintegration and release of active agent from the film. The rate of disintegration of the film and release of the active agent from the film within the conditions of the oral cavity maximizes the absorption of the active agent through the oral mucosa.

According to certain embodiments, said oral film comprises at least about 45 weight percent of at least one water soluble film forming polymer, based on the weight of the dry film, and an active agent.

According to other embodiments, the oral film comprises a mixture of a polyalkylene oxide and a cellulose polymer, wherein the ratio of said polyalkylene oxide to said cellulose polymer present in said film is about 1:2 to about 1:5, and an active agent.

According to further embodiments, the oral film comprises at least one water soluble film forming polymer and an active agent, wherein said oral film maintains at least partial integrity and active agent release capability after in vitro exposure to artificial human saliva solution for at least 15 minutes.

A method for preparing a slow disintegrating oral film from at least one water soluble film forming polymer and an active agent is provided.

According to certain embodiments, the method for preparing a slow disintegrating oral film comprises mixing together at least one water soluble film forming polymer, an active agent and a solvent to form a mixture; and forming a film from the mixture, wherein said film comprises at least 45 weight percent of said at least one water soluble film forming polymer, based on the total weight of the dry film.

According to other embodiments, the method for preparing a slow disintegrating oral film comprises mixing together at least one polyalkylene oxide polymer, at least one cellulose polymer, and an active agent to form a mixture; and forming a film from the mixture, wherein the ratio of said polyalkylene oxide polymer to said cellulose polymer present in said dry film is about 1:2 to about 1:5 (wt/wt).

According to further embodiments, the method for preparing a slow disintegrating oral film comprises mixing together at least one water soluble film forming polymer and an active agent to form a mixture; and forming a film from the mixture, wherein said oral film maintains at least partial integrity and active agent release capability after in vitro exposure to artificial human saliva solution for at least 15 minutes.

A method of using a slow disintegrating oral film to administer an effective amount of an active agent to the oral cavity is further provided.

According to certain embodiments, the method of administering an active agent comprises providing a slow disintegrating oral film comprising least 45 weight percent of at least one water soluble film forming polymer, based on the weight of the dry film, and an active agent; and introducing said film into the oral cavity.

According to other embodiments, the method of administering an active agent comprises providing a slow disintegrating film comprising a mixture of a polyalkylene oxide and a cellulose polymer, wherein the ratio of said polyalkylene oxide to said cellulose polymer present in said dry film is about 1:2 to about 1:5 (wt/wt), and an active agent; and introducing said film into the oral cavity.

According to further embodiments, the method of administering an active agent comprises providing a slow disintegrating oral film comprising at least one water soluble film forming polymer and an active agent, wherein said oral film maintains at least partial integrity and active agent release capability after in vitro exposure to artificial human saliva solution for at least 15 minutes, and introducing said film into the oral cavity.

DETAILED DESCRIPTION

Figure 1:
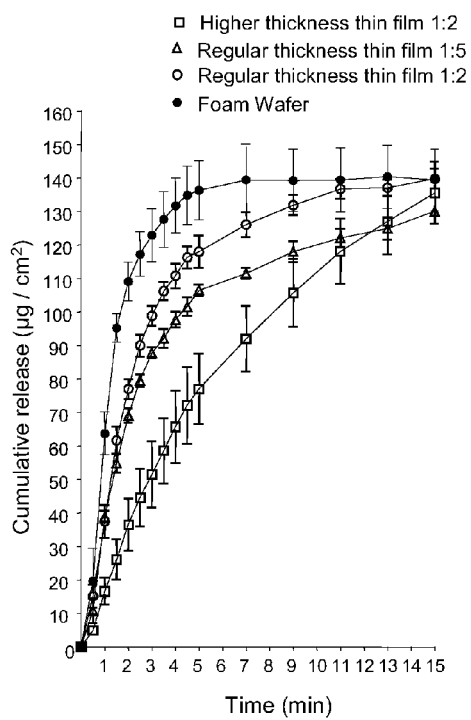
FIG. 1 is a graph showing the results of an in vitro release of nicotine from three different oral film as compared to a release of nicotine from a prior art film.

The invention relates to a slow disintegrating thin film for delivering and releasing a cosmetically active agent, or pharmacologically active agent to the oral cavity for absorption through the oral mucosa. According to certain embodiments, the oral film compositions for the delivery and release of an active agent contains a nicotine active for delivery and release into the oral cavity of an individual so that the nicotine active is absorbed through the oral mucosa and directly enters the individual's systemic circulation.

The dosage form may be a monolayer or multi-layer mucoadhesive film, which comprises at least one water soluble film forming polymer and an effective amount of an active agent. The mucoadhesive film disintegrates when applied to the oral cavity to release the active agent, which is then absorbed through the oral mucosa and directly reaches systemic circulation.

According to certain embodiments, the oral film comprises at least about 45 weight percent of one or more water soluble film forming polymers, based on the total weight of the dry film. The disintegrable thin film includes a pharmacologically active agent that is compatible with the water soluble film forming polymer(s). The active agent incorporated into the oral film is released upon disintegration of the film and can be absorbed through the oral mucosa. The composition of the disintegrable oral film is such that the oral film has a disintegration time in the oral cavity of greater than 30 seconds and as much as 15 or more minutes. "Disintegration time" is the time in which the integral oral film breaks down and is no longer recognized as an integral unit after being brought into contact with saliva, water, or similar solvent. The integral dosage unit maintains partial integrity and active agent release capability for at least 15 minutes after exposure to artificial human saliva solution.

The oral film comprises at least one water soluble film forming polymer. Water soluble film forming polymers that are suitable for use in the present invention include, but are not limited to, cellulose, cellulose derivatives, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullulan, polyvinyl pyrrolidone, polyvinyl alcohol, alginic acid, polyethylene glycol-polyvinyl alcohol copolymers, salts of alginic acid, carboxyvinyl polymers, and mixtures thereof.

Without limitation, suitable cellulose derivatives include alkyl celluloses, such as methyl cellulose and ethyl cellulose, substituted alkyl celluloses, such as hydroxyethyl cellulose, hydroxypropyl cellulose, hydroxypropyl methylcellulose, carboxymethyl cellulose, salts of substituted alkyl celluloses, such as sodium carboxymethyl cellulose, and mixtures thereof.

Without limitation, suitable gums include xanthan gum, tragacanth gum, guar gum, acacia gum, arabic gum, and mixtures thereof.

The slow disintegrating oral film may comprise a mixture of polyethylene oxide and hydroxypropyl methylcellulose as the water soluble film forming polymers. The film forming polymers polyethylene oxide and hydroxypropyl methylcellulose may be present in the dry film in an amount greater than 45 weight percent, based on the total weight of the dry oral film.

According to certain embodiments, the film forming polymers polyethylene oxide and hydroxypropyl methylcellulose may be present in the dry film in an amount from greater than 45 weight percent to about 90 weight percent, based on the total weight of the dry oral film. According to other embodiments, the film forming polymers polyethylene oxide and hydroxypropyl methylcellulose may be present in the dry film in an amount from greater than 45 weight percent to about 75 weight percent, based on the total weight of the dry oral film. According to further embodiments, the film forming polymers polyethylene oxide and hydroxypropyl methylcellulose may be present in the dry film in an amount from greater than 45 weight percent to about 50 weight percent, based on the total weight of the dry oral film.

According to certain embodiments, the disintegrable oral film comprises a blend or mixture of a polyalkylene oxide, a cellulose polymer and the active agent. The weight ratio of the polyalkylene oxide to cellulose polymer in the dry film may be about 1:2 to about 1:5.

According to certain illustrative embodiments, the disintegrable oral film comprises a mixture of polyethylene oxide and hydroxypropyl methylcellulose. Without limitation, a suitable polyethylene oxide polymer for use in the oral film is commercially available from The Dow Chemical Company under the trademark POLYOX. POLYOX polyethylene oxide polymers are non-ionic, film forming water soluble polymers that may be calendered, extruded, injection molded or cast. The molecular weights of the POLYOX polyethylene oxide polymers range from about 100,000 to about 8,000,000. Without limitation, a particularly suitable POLYOX polymer that may used in the oral film is POLYOX N-80. POLYOX N-80 has an approximate molecular weight of 200,000 and a viscosity of about 65 to about 115 mPa/s (5% aqueous solution at 25° C.).

Without limitation, suitable hydroxypropyl methylcellulose polymers for use in the oral film are commercially available from The Dow Chemical Company under the trademark METHOCEL. A particularly suitable METHOCEL polymer that may used in the oral film is METHOCEL E50. METHOCEL E50 is a hydroxypropyl methylcellulose polymer having an approximate molecular weight of 30,000.

A special embodiment of the invention is characterized by a disintegrable oral film comprising: at least 45 weight percent of at least one water soluble film forming polymer, based on the total weight of the dry film; and an active agent, wherein said disintegrable oral film comprises a mixture of a polyalkylene oxide, preferably polyethylene oxide, and a cellulose polymer, preferably hydroxypropyl methylcellulose.

The oral film is used to deliver and release a wide variety of active agents to the oral cavity. The term "active agents" includes cosmetically or pharmacologically active agents which may be delivered to the oral cavity. Non-limiting examples of suitable active agents include tooth whitening materials, breath fresheners, anti-cavity compounds, anti-calculus compounds, anti-anginals, anti-anxiety, anti-oxidants, anti-convulsants, anti-diabetic agents, anti-diarrheal agents, anti-epileptic agents, anti-inflammatory agents, anti-psychotic agents, anti-pyretic agents, anti-spasmodic agents, analgesics, antihistamines, local anesthetics, anti-bacterial compounds, disinfectants, vasoconstrictors, hemostatics, chemotherapeutics, antibiotics, tooth desensitizing agents, anti-fungals, vasodilators, anti-hypertensives, anti-migraine, anti-arrhythmics, anti-asthmatics, anti-depressants, cardiac agents, calcium antagonists, central nervous system actives, cold remedies, cough remedies, decongestants, diuretics, nicotine, vaccines, peptides or prodrugs, hormones, proton pump inhibitors, H2 receptor antagonists, vitamins and other dietary and nutritional supplements. The above list of active agents is merely provided to illustrate the types of active agents which may be incorporated into the oral film. It should be noted, however, that any other compatible cosmetically or pharmacologically active agent or combinations of agents may be included in the slow disintegrating oral film.

The above list of active agents has been described in connection with preparation of oral films for delivery of cosmetically and pharmacologically active agents humans. However, it is within the scope of the present invention to incorporate cosmetically or pharmacologically active veterinary agents into the slow disintegrating oral films for delivery to non-human animals.

According to certain embodiments, the oral film comprises at least one water soluble film forming polymer and a nicotine active as the active agent. The term "nicotine active" refers free nicotine base, nicotine derivatives, nicotine salts, salts of nicotine derivatives, nicotine complexes, and combinations or mixtures thereof. A variety of nicotine actives are well known in the art and are commercially available.

Nicotine salts include any physiologically acceptable salt, such as hydrochloride, dihydrochloride, sulfate, tartrate, bitartrate, zinc chloride, salicylate, alginate, ascorbate, benzoate, citrate, edetate, fumarate, lactate, maleate, oleate and sorbate, formed by the interaction of nicotine and any acid. Particularly useful nicotine salts include but are not limited to, nicotine monotartrate, nicotine bitartrate, nicotine hydrochloride, nicotine dihydrochloride, nicotine sulfate, nicotine zinc chloride monohydrate, nicotine salicylate, and mixtures thereof.

Suitable nicotine complexes include, but are not limited to, nicotine oils, nicotine complexed with cyclodextrin, nicotine complexed with polymer resins, and combinations or mixtures thereof.

The slow disintegrating oral films comprise at least one nicotine active in an amount sufficient to reduce or alleviate nicotine cravings. The phrase "at least one nicotine active" refers to an oral film comprising one nicotine active, or a mixture of more than one nicotine active. In certain embodiments, the amount of nicotine active included in the oral film is from about 0.25 mg to about 10 mg per dose unit.

According to certain embodiments, the amount of the nicotine active included in the oral film is from about 0.25 to about 6 mg per dose unit. According to other embodiments, the amount of nicotine active included in the oral film is from about 0.25 to about 4 mg per dosage unit. According to further embodiments, the amount of nicotine active included in the oral film is from about 1 to about 3 mg per dosage unit.

The disintegrable oral films may contain one or more of the following optional components: taste modifying agents, bioadhesive agents, buffering agents, coloring agents, stabilizing agents, inert fillers, emulsifying agents, permeation enhancers, pH adjusting agents, plasticizers, and preservatives.

Without limitation, suitable taste modifying agents for use in the disintegrable oral film include flavorants, sweeteners, taste-masking agents, and mixtures thereof. Suitable taste modifying agents include, but are not limited to, the essential oils or water soluble extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, green tea, grapefruit, banana, butter, chamomile, sugar, dextrose, lactose, mannitol, sorbitol, sucrose, sucralose, xylitol, malitol, aspartame, saccharin, sodium saccharin, sodium cyclamate, acesulfame K, and honey.

Without limitation, suitable colorants for use in the disintegrable oral film include pigments, dyes, natural food colors that are suitable for food and drug applications, such as FD&C coloring agents, and mixtures thereof.

Without limitation, suitable stabilizing agents for use in the oral thin films include chelating agents. Chelating agents are used to prevent oxidation of the disintegrable oral film. A particularly useful chelating agent is ethylenediaminetetraacetic acid (EDTA). Any chelating agents that can be incorporated into a solid pharmaceutical preparation may be utilized in the oral film.

The oral film compositions may optionally include one or more water soluble inert fillers. Without limitation, suitable water soluble inert fillers for use in the disintegrable oral film include mannitol, xylitol, glucose, fructose, sucrose, sucralose, lactose, trehalose, maltodextrin, dextran, dextrin, modified starches, dextrose, sorbitol, dextrates, and mixtures thereof.

Without limitation, suitable emulsifying agents for use in the disintegrable oral film include solubilizers, wetting agents, and release modifiers. Suitable emulsifying agents include, but are not limited to, castor oil derivatives, cetyl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polysorbates, and mixtures thereof.

The oral film compositions may optionally include at least one plasticizer. Suitable plasticizers which may be included in the film composition include, but are not limited to, alkylene glycols, polyalkylene glycols, glycerol, triacetin, deacetylated monoglyceride, diethyl salate, triethyl citrate, dibutyl sebacate, polyethylene glycols, and the like, and mixtures thereof.

The oral films may also optionally include one or more "permeation enhancers." A "permeation enhancer" is a natural or synthetic compound which facilitates the absorption of an active agent through a mucosal surface. The phrase "one or more" is intended to mean that a single permeation enhancer, or combinations or mixtures of more than one permeation enhancer, may be included in the oral film.

The oral film composition may also include one or more preservatives. Suitable preservative include, but are not limited to, butylated hydroxyanisole (BHA), butylate hydroxytoluene (BHT), ascorbic acid, tocopherol derivatives, citric acid, parabens, derivatives of parabens, sorbic acid, salts of sorbic acid, sodium benzoate, propionic acid, salts of propionic acid, acetic acid, salts of acetic acid, and mixtures thereof.

Methods for preparing the disintegrable oral film are described. According to certain embodiments, the method for preparing a disintegrable oral film includes mixing together at least one water soluble film forming polymer, an active agent, a compatible solvent, and optionally any one or more of the above described optional components to form a homogenous mixture. A film is formed from the mixture of water soluble film forming polymer(s), active agent and optional components to provide a disintegrable oral film containing at least 45 percent by weight of said water soluble polymer(s), based on the total weight of the dry film.

According to other embodiments, the method for preparing a disintegrable oral film includes mixing together at least one polyalkylene oxide polymer, at least one cellulose polymer, an active agent, a compatible solvent, and any optionally one or more of the above described optional components to form a homogenous mixture. A film is formed from this mixture. The water polymer polymers are combined together to provide a ratio of said polyalkylene oxide polymer to cellulose polymer in the dry film of about 1:2 to about 1:5 (wt/wt).

The homogenous mixture of film components is degassed and uniformly coated onto a casting substrate at a predetermined thickness and then dried. Alternatively, the homogenous mixture may be extruded to form a film on a casting substrate The dried film prepared from casting or extrusion is cut into various sizes to produce individual dosage units. The dried film may be cut by any known cutting method, such as, for example, die cutting, knife cutting, or machine cutting.

Methods of using the disintegrable film for administering an effective dosage of an active agent to the oral cavity of an individual is also provided. According to illustrative embodiments, the method includes using the disintegrable film to administer an effective dosage of nicotine to the oral cavity of an individual who desires to stop using tobacco products.

The thin film dosage form is applied to the oral cavity and adheres to a mucosal surface, such as the cheek, palate, or tongue as soon as the individual closes his or her mouth. The film disintegrates and releases the nicotine active for absorption through the oral mucosa. For example, the active may be absorbed by the sublingual or buccal mucosa. The oral film has a high mucoadhesivity to the oral mucosa and slow disintegration rate. Because of the high mucoadhesivity and slow disintegration rate, the nicotine active is absorbed substantially at the point of adhesion within the oral cavity. Because the nicotine active is absorbed through the oral mucosa, the amount of nicotine active that is swallowed is minimized. The release of nicotine from the thin film occurs without mastication, such as chewing or sucking of the film. There is virtually no risk that an individual will choke or accidentally swallow the whole dosage form, which may occur with nicotine-containing tablets, capsules or lozenges.

EXAMPLES

The following examples are set forth to further illustrate the oral films and methods of preparation. The below examples, however, should not be construed as limiting the present invention in any manner.

Example 1

A single layer disintegrable oral film was produced by preparing a casting solution and casting a thin film from the casting solution. The oral film comprised a mixture of POLYOX N80 and METHOCEL E50 at a weight ratio of 1:2.

Preparation of the Casting Solution 451 g of deionized water was placed into a stainless steel pot and heated on a hot plate to 80° C. with mixing. To the water solution, 0.03 g of FD&C blue coloring agent, 23.55 g of POLYOX N80 and 47.14 g of METHOCEL E50 and were added and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath and a menthol solution (10.56 g of menthol in ethanol), 7.54 g of glycerin, 1.95 g of sucralose, 49.53 g of peppermint flavor, and ethyl alcohol was added with mixing. A nicotine solution was prepared by adding 4.01 g of nicotine bitartrate to 20 ml of deionized water. The nicotine bitartrate solution was added to the thin film casting solution.

Casting the Thin Film

The casting solution was coated on a polyvinyl chloride casting liner and was dried at a temperature of about 70° C. for about 4 minutes. The resulting disintegrable thin film contained 1 mg of nicotine in 484 mm². The table below indicates the weight percent of each component in the dry film.

| Ingredient | % in Dry Film |
| --- | --- |
| Polyox ™ N-80 (Dow) | 16.32 |
| Methocel ™ E50 (Dow) | 32.67 |
| MENTHOL | 7.32 |
| Nicotine bitartrate | 2.78 |
| Glycerin | 5.22 |
| Peppermint Flavor | 34.32 |
| Sucralose | 1.35 |
| FD&C Blue | 0.02 |

Example 2

A single layer disintegrable oral film was produced by preparing a casting solution and casting a thin film from the casting solution. The oral film comprised a mixture of POLYOX N80 and METHOCEL E50 at a ratio of 1:3.

Preparation of the Casting Solution 300 g of deionized water was placed into a stainless steel pot and heated on a hot plate to 80° C. with mixing. To the water solution, 0.02 g of FD&C blue coloring agent, 11.77 g of POLYOX N80 and 35.30 g of METHOCEL E50 and were added and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath and a menthol solution (7 g of menthol in ethanol), 5 g of glycerin, 1.3 g of sucralose, 33 g of peppermint flavor, and ethyl alcohol was added with mixing. A nicotine solution was prepared by adding 6.63 g of nicotine bitartrate to 30 ml of deionized water. The nicotine bitartrate solution was added to the thin film casting solution.

Casting the Thin Film

The casting solution was coated on a siliconized casting liner at a coating wet thickness of 0.62 mm, and was dried at a temperature of about 70° C. for about 4 minutes. The resulting disintegrable thin film contained 1 mg of nicotine in 484 mm². The table below indicates the weight percent of each component in the dry film.

| Ingredient | % in Dry Film |
| --- | --- |
| Polyox ™ N-80 | 11.77 |
| Methocel ™ E50 | 35.3 |
| Menthol | 7 |
| Nicotine bitartrate | 6.63 |
| Glycerin | 5 |
| Peppermint Flavor | 33 |
| Sucralose | 1.3 |
| FD&C Blue | 0.02 |

Example 3

A single layer disintegrable oral film was produced by preparing a casting solution and casting a thin film from the casting solution. The oral film comprised a mixture of POLYOX N80 and METHOCEL E50 at a ratio of 1:4.

Preparation of the Casting Solution 300 g of deionized water was placed into a stainless steel pot and heated on a hot plate to 80° C. with mixing. To the water solution, 0.02 g of FD&C blue coloring agent, 9.41 g of POLYOX N80 and 37.65 g of METHOCEL E50 and were added and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath and a menthol solution (7 g of menthol in ethanol), 5 g of glycerin, 1.3 g of sucralose, 33 g of peppermint flavor, and ethyl alcohol was added with mixing. A nicotine solution was prepared by adding 6.63 g of nicotine bitartrate to 30 ml of deionized water. The nicotine bitartrate solution was added to the thin film casting solution.

Casting the Thin Film

The casting solution was coated on a siliconized casting liner at a coating wet thickness of 0.62 mm, and was dried at a temperature of about 70° C. for about 4 minutes. The resulting disintegrable thin film contained 1 mg of nicotine in 484 mm². The table below indicates the weight percent of each component in the dry film.

| Ingredient | % in Dry Film |
| --- | --- |
| Polyox ™ N-80 | 9.41 |
| Methocel ™ E50 | 37.65 |
| Menthol | 7 |
| Nicotine bitartrate | 6.63 |
| Glycerin | 5 |
| Peppermint Flavor | 33 |
| Sucralose | 1.3 |
| FD&C Blue | 0.02 |

Example 4

A single layer disintegrable oral film was produced by preparing a casting solution and casting a thin film from the casting solution. The oral film comprised a mixture of POLYOX N80 and METHOCEL E50 at a ratio of 1:5 (wt/wt).

Preparation of the Casting Solution 300 g of deionized water was placed into a stainless steel pot and heated on a hot plate to 80° C. with mixing. To the water solution, 0.02 g of FD&C blue coloring agent, 7.84 g of POLYOX N80 and 39.22 g of METHOCEL E50 and were added and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath and a menthol solution (7 g of menthol in ethanol), 5 g of glycerin, 1.3 g of sucralose, 33 g of peppermint flavor, and ethyl alcohol was added with mixing. A nicotine solution was prepared by adding 6.63 g of nicotine bitartrate to 30 ml of deionized water. The nicotine bitartrate solution was added to the thin film casting solution.

Casting the Thin Film

The casting solution was coated on a siliconized casting liner at a coating wet thickness of 0.585 mm, and was dried at a temperature of about 70° C. for about 4 minutes. The dry coat weight of the film was 0.956 g. The resulting disintegrable thin film contained 1 mg of nicotine in 484 mm². The table below indicates the weight percent of each component in the dry film.

| Ingredient | % in Dry Film |
| --- | --- |
| Polyox ™ N-80 | 7.84 |

-continued

| Ingredient | % in Dry Film |
| --- | --- |
| Methocel ™ E50 | 39.22 |
| MENTHOL | 7 |
| Nicotine bitartrate | 6.63 |
| Glycerin | 5 |
| Peppermint Flavor | 33 |
| Sucralose | 1.3 |
| FD&C Blue | 0.02 |

Example 5

A single layer disintegrable oral film was produced by preparing a casting solution and casting a thin film from the casting solution. The oral film comprised a mixture of POLYOX N80 and METHOCEL E50 at a ratio of 1:2.

Preparation of the Casting Solution 458 g of deionized water was placed into a stainless steel pot and heated on a hot plate to 80° C. with mixing. To the water solution, 0.03 g of FD&C blue coloring agent, 23.58 g of POLYOX N80 and 47.12 g of METHOCEL E50 and were added and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath and a menthol solution (10.57 g of menthol in ethanol), 7.52 g of glycerin, 1.95 g of sucralose, 49.51 g of peppermint flavor, and ethyl alcohol was added with mixing. A nicotine solution was prepared by adding 9.94 g of nicotine bitartrate to 30 ml of deionized water. The nicotine bitartrate solution was added to the thin film casting solution.

Casting the Thin Film

The casting solution was coated on a siliconized casting liner at a coating wet thickness of 0.70 mm, and was dried at a temperature of about 70° C. for about 4 minutes. The dry coat weight of the film was 1.034 g. The resulting disintegrable thin film contained 1 mg of nicotine in 600 mm². The table below indicates the weight percent of each component in the dry film.

| Ingredient | % in Dry Film |
| --- | --- |
| Polyox ™ N-80 | 15.7 |
| Methocel ™ E50 | 31.37 |
| Menthol | 7.04 |
| Nicotine bitartrate | 6.62 |
| Glycerin | 5.01 |
| Peppermint Flavor | 32.96 |
| Sucralose | 1.3 |
| FD&C Blue | 0.02 |

Examples 6-8

In Vitro Drug Release

A 1.54 cm² size samples of oral films were placed on a Franz cell with a teflon filter as a support. An artificial human saliva solution was prepared from 0.19 g/L $K_2PO_4$, 2.38 g/L $Na_2HPO_4$ and 8 g/L of NaCl in water. Approximately 8 ml of artificial saliva solution buffered at pH 7.4 with HEPES 25 mM and maintained as 37° C., was introduced into the test Franz cell.

The experiment was started by placing the artificial saliva in contact with the oral film. 1 ml samples of the artificial saliva solution were taken every 30 seconds for 15 minutes. The removed artificial saliva volume (1 ml) was replenished with fresh artificial saliva solution after each sample. The quantities of nicotine released by the oral film was determined by HPLC analysis of the collected samples. A total of three measurements were made per formulation. The results of the in vitro drug release experiments are shown in FIG. 1.

Example 8

In Vitro Buccal Mucosa Permeation

In vitro buccal mucosa permeation studies were performed at 35° C. in Franz cells using porcine buccal mucosa tissue. Fresh porcine buccal mucosa tissue was obtained and frozen at −80° C. Immediately prior to use, the porcine buccal mucosa tissue was dermatomed to a thickness of 0.8 mm.

Figure 2:
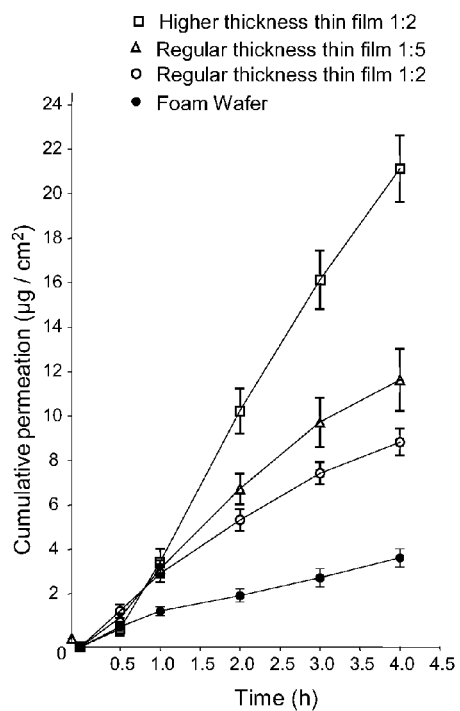
FIG. 2 is a graph showing the results of an in vitro mucosa permeation test.

Approximately 8 ml of artificial saliva solution buffered at pH 7.4 with 25 mM HEPES was added to the Franz cell. A test sample of the oral film was placed in the Franz cell. The porcine mucosal tissue was placed in the Franz cell and was brought into contact with the oral film. The experiment was started when the artificial saliva solution was put into contact with the oral film. After 3 minutes, the artificial saliva solution was removed and the Franz cell was washed with distilled water. 0.75 ml of fresh artificial saliva solution and approximately 8 ml of phosphate buffered saline (PBS) was added to the Franz cell. Samples of the solution were withdrawn from the Franz cell at various time intervals, namely, 0, 0.5, 1, 2, 3 and 4 hours. The removed solution volume (1 ml) was replenished with an equal amount of fresh solution after each withdrawal. The quantities of nicotine released after 3 minutes and permeating the mucosa were determined by HPLC of the collected samples. The results of the in vitro buccal permeation experiments are shown in FIG. 2.

Example 9

Additional thin film prototypes were prepared from formulations (A), (B) and (C) comprising Methocel™ E50 and E5 grades of HPMC in fixed amounts; and the effect of a gum such as xantham gum on in vitro disintegration time was evaluated.

|  | (A) | (B) | (C) |
| --- | --- | --- | --- |
| Methocel ™ E50 | 6.60 | 6.60 | 6.60 |
| Methocel ™ E5 | 13.20 | 13.20 | 13.20 |
| Xanthan Gum (Xantural ® 180, CP Kelko) | 0.00 | 2.00 | 4.00 |
| Total dry weight | 19.80 | 21.80 | 23.80 |

In vitro disintegration time. All three formulations, when contacted with human saliva, were transformed into a bioadhesive gel within a few seconds. (A) disintegrated in a few seconds; (B) in 4 minutes; and (C) in 8 minutes. Thus, the addition of xanthan gum was found to lengthen time to disintegration. (B) is a preferred formulation for delivering nicotine active to the oral cavity.

Example 10

Thin film prototypes according to the invention can also be prepared comprising hydroxypropyl methylcellulose as the film forming polymer and arabic gum. For example, arabic gum can be substituted for xantham gum in formulations (A), (B) and (C) above, to provide similar disintegration profiles.

The disintegrable oral films are useful as a nicotine replacement therapy. The oral films are useful as a means to reduce or stop tobacco usage, such as stopping the smoking cigarettes, cigars, pipe tobacco, stopping the use of smokeless chewing tobacco. The oral films may be used concurrently with tobacco in any planned tobacco reduction program. Thus, the present invention also relates to methods of reducing tobacco usage, comprising orally administering one or more of the orally dissolving films of the present invention to a person in need of such reduction. In general, the disintegrable oral films may be administered to an individual as needed to prevent or reduce nicotine cravings, within any recommended or permitted limits. The orally dissolving films are typically administered such that the nicotine active is primarily delivered transbuccally in the mouth.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

We claim:

1. A dry oral film that is disintegrable in saliva and that has mucoadhesivity to the oral mucosa consisting of:
   a) at least 45 weight percent (based on the total weight of the dry film) of at least one water soluble film-forming polymer selected from the group consisting of cellulose, cellulose derivatives, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullulan, polyvinyl pyrrolidone, polyvinyl alcohol, alginic acid, polyethylene glycol-polyvinyl alcohol copolymers, salts of alginic acid, and carboxyvinyl polymers;
   b) a nicotine active; and, optionally,
   c) one or more compounds selected from the group consisting of taste-modifying agents, bioadhesive agents, coloring agents, stabilizing agents, inert fillers, emulsifying agents, permeation enhancers, plasticizers, and preservatives;
   wherein component (c) is not a pH adjusting agent or buffering agent, and
   wherein the film maintains at least partial integrity and active agent release capability after in vitro exposure to artificial human saliva solution for at least 15 minutes.

2. The film of claim 1, wherein the film comprises from about 45 to about 90 weight percent of the film forming polymer.

3. The film of claim 1, wherein the film comprises a mixture of two different water soluble film forming polymers.

4. The film of claim 3, wherein the two polymers are polyalkylene oxide and a cellulose.

5. The film of claim 4, wherein the polyalkylene oxide is polyethylene oxide and the cellulose polymer is hydroxypropyl methylcellulose.

6. The film of claim 5, wherein the ratio of polyethylene oxide to hydroxypropyl methylcellulose is from about 1:2 to about 1:5 (wt/wt).

7. The film of claim 6, wherein the ratio of polyethylene oxide to hydroxypropyl methylcellulose is about 1:2.

8. The film of claim 6, wherein the ratio of polyethylene oxide to hydroxypropyl methylcellulose is about 1:3.

9. The film of claim 6, wherein the ratio of polyethylene oxide to hydroxypropyl methylcellulose is about 1:4.

10. The film of claim 6, wherein the ratio of polyethylene oxide to hydroxypropyl methylcellulose is about 1:5.

11. The film of claim 1, component c) is present and one of said component is a gum.

12. The film of claim 2 which comprises hydroxypropyl methylcellulose and xanthan gum.

13. The film of claim 1, wherein the nicotine active comprises free nicotine base, nicotine derivatives, nicotine complexes, nicotine salts, or mixtures thereof.

14. The film of claim 1, wherein the nicotine active is nicotine bitartrate.

15. A dry oral film that is disintegrable in saliva and that has mucoadhesivity to the oral mucosa consisting of:
   a) at least 45 weight percent of a mixture of a polyalkylene oxide and a cellulose polymer, wherein the ratio of polyalkylene oxide to cellulose polymer is about 1:2 to about 1:5 (wt/wt);
   b) a nicotine active; and, optionally,
   c) one or more compounds selected from the group consisting of taste-modifying agents, bioadhesive agents, coloring agents, stabilizing agents, inert fillers, emulsifying agents, permeation enhancers, plasticizers, and preservatives;
   wherein component (c) is not a pH adjusting agent or buffering agent.

16. The film of claim 15, wherein the polyalkylene oxide is polyethylene oxide and the cellulose polymer is hydroxypropyl methylcellulose.

17. The film of claim 16, wherein the ratio of polyethylene oxide to hydroxypropyl methylcellulose is about 1:2.

18. The film of claim 16, wherein the ratio of polyethylene oxide to hydroxypropyl methylcellulose is about 1:3.

19. The film of claim 16, wherein the ratio of polyethylene oxide to hydroxypropyl methylcellulose is about 1:4.

20. The film of claim 16, wherein the ratio of polyethylene oxide to hydroxypropyl methylcellulose is about 1:5.

21. The film of claim 15, wherein the nicotine active comprises free nicotine base, nicotine derivatives, nicotine complexes, nicotine salts, or mixtures thereof.

22. The film of claim 21, wherein the nicotine active is nicotine bitartrate.

23. The film of claim 15, wherein the film maintains at least partial integrity and active agent release capability after in vitro exposure to artificial human saliva solution for at least 15 minutes.

24. A dry oral film that is disintegrable in saliva and has mucoadhesivity to the oral mucosa consisting of:
   a) at least 45 weight percent of a mixture of a polyalkylene oxide and a cellulose polymer, wherein the ratio of polyalkylene oxide to cellulose polymer is about 1:2 to about 1:5;
   b) nicotine bitartrate; and, optionally,
   c) one or more compounds selected from the group consisting of taste-modifying agents, bioadhesive agents, coloring agents, stabilizing agents, inert fillers, emulsifying agents, permeation enhancers, plasticizers, and preservatives;

wherein the film maintains at least partial integrity and active agent release capability after in vitro exposure to artificial human saliva solution for at least 15 minutes, wherein component (c) is not a pH adjusting agent or buffering agent.

25. A dry oral film that is disintegrable in saliva and that has mucoadhesivity to the oral mucosa consisting of:
   a) at least 45 weight percent of a mixture of a polyalkylene oxide and a cellulose polymer, wherein the ratio of polyalkylene oxide to cellulose polymer in the film is about 1:2 to about 1:5 (wt/wt);
   b) a nicotine active;
   c) a gum; and, optionally,
   d) one or more of one or more compounds selected from the group consisting of taste-modifying agents, bioadhesive agents, coloring agents, stabilizing agents, inert fillers, emulsifying agents, permeation enhancers, plasticizers, and preservatives;
   wherein the film maintains at least partial integrity and active agent release capability after in vitro exposure to artificial human saliva solution for at least 15 minutes,
   wherein component (d) is not a pH adjusting agent or buffering agent.

26. The film of claim 25, wherein the polyalkylene oxide is polyethylene oxide, the cellulose polymer is hydroxypropyl methylcellulose, and the gum is xanthan gum.

27. The film of claim 26, wherein the nicotine active is nicotine bitartrate.

28. A dry oral film that is disintegrable in saliva and that has mucoadhesivity to the oral mucosa wherein the film has a disintegration time in the oral cavity of greater than 30 seconds, wherein the film consists of:
   a) at least 45 weight percent (based on the total weight of the dry film) of at least one water soluble film-forming polymer selected from the group consisting of cellulose, cellulose derivatives, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullulan, polyvinyl pyrrolidone, polyvinyl alcohol, alginic acid, polyethylene glycol-polyvinyl alcohol copolymers, salts of alginic acid, and carboxyvinyl polymers;
   b) a nicotine active; and, optionally,
   c) one or more compounds selected from the group consisting of taste-modifying agents, bioadhesive agents, coloring agents, stabilizing agents, inert fillers, emulsifying agents, permeation enhancers, plasticizers, and preservatives,
   wherein component (c) is not a pH adjusting agent or buffering agent.

29. The film of claim 28, wherein the film maintains at least partial integrity and active agent release capability after in vitro exposure to artificial human saliva solution for at least 15 minutes.

30. The film of claim 28 which comprises a mixture of polyalkylene oxide and a cellulose polymer.

31. The film of claim 28 comprising a gum.

32. The film of claim 15, wherein the polyalkylene oxide has a molecular weight of about 100,000 to about 8,000,000.

33. The film of claim 24, wherein the polyalkylene oxide has a molecular weight of about 100,000 to about 8,000,000.

34. The film of claim 25, wherein the polyalkylene oxide has a molecular weight of about 100,000 to about 8,000,000.

* * * * *